United States Patent
Inazuru (10) Patent No.: US 7,298,826 B2
(45) Date of Patent: Nov. 20, 2007

(54) X-RAY GENERATOR

(75) Inventor: Tutomu Inazuru, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/513,610

(22) PCT Filed: Apr. 25, 2003

(86) PCT No.: PCT/JP03/05387

§ 371 (c)(1),
(2), (4) Date: Nov. 5, 2004

(87) PCT Pub. No.: WO03/096763

PCT Pub. Date: Nov. 20, 2003

(65) Prior Publication Data

US 2005/0163284 A1 Jul. 28, 2005

(30) Foreign Application Priority Data

May 9, 2002 (JP) .............................. 2002-134488

(51) Int. Cl.
*H01J 35/06* (2006.01)
(52) U.S. Cl. ...................... 378/136; 378/108; 378/109; 378/111; 378/113; 378/138
(58) Field of Classification Search ........ 378/108–109, 378/119, 121–122, 140, 151, 161, 111, 113, 378/136, 138
See application file for complete search history.

(56) References Cited

U.S. PATENT DOCUMENTS

| | | | | |
|---|---|---|---|---|
| 5,550,886 A | * | 8/1996 | Dobbs et al. ................. 378/19 |
| 5,729,583 A | * | 3/1998 | Tang et al. ................. 378/122 |
| 6,137,860 A | * | 10/2000 | Ellegood et al. .............. 378/58 |
| 6,320,935 B1 | * | 11/2001 | Shinar et al. ............... 378/119 |
| 6,333,968 B1 | * | 12/2001 | Whitlock et al. .......... 378/136 |
| 6,490,341 B1 | | 12/2002 | Ochiai et al. |
| 6,542,576 B2 | * | 4/2003 | Mattson ..................... 378/119 |
| 6,639,969 B2 | | 10/2003 | Ochiai et al. |

FOREIGN PATENT DOCUMENTS

EP 432568 6/1991

(Continued)

OTHER PUBLICATIONS

Shimizu, English translation of JP 59-37453, Feb. 29, 1984, USPTO document No. PTO 06-2353, Translation prepared Feb. 2006, McElroy Translation Company.*

*Primary Examiner*—Edward J. Glick
*Assistant Examiner*—John M Corbett
(74) *Attorney, Agent, or Firm*—Drinker Biddle & Reath LLP (57) ABSTRACT

An X-ray generator of this invention has an X-ray monitor that monitors a state of an X-ray emitted from a target. Hence the state of the X-ray can be monitored in real time to maintain the X-ray in a constant state. The X-ray monitor is positioned off the path on which an X-ray transmitted from a first exit window travels. Hence, when the X-ray is emitted from the first exit window to an object to be inspected, the X-ray monitor does not obstruct the approaching of the object to the first exit window. This makes it possible to acquire X-ray images of high magnification.

1 Claim, 7 Drawing Sheets

FOREIGN PATENT DOCUMENTS

| | | |
|---|---|---|
| JP | 54-013316 | 1/1979 |
| JP | 55-124997 | 9/1980 |
| JP | 59-037453 | 2/1984 |
| JP | 61-032998 | 2/1986 |
| JP | 5-303999 | 11/1993 |
| JP | 9-184900 | 7/1997 |

* cited by examiner

X-RAY GENERATOR

TECHNICAL FIELD

This invention relates to an X-ray generator for irradiating a target with an electron beam to generate X-rays.

BACKGROUND ART

The inspection device which irradiates an object to be inspected with X-rays and taking an image of the X-rays transmitted through the object has been known previously. An X-ray generator can be used as an X-ray source for such an inspection device. The X-ray generator generates X-rays by irradiating a target with an electron beam. The X-ray dosage varies according to the acceleration voltage applied to the electron beam, the current value of the electron beam or the like, as well as according to the damage of the target, the thermal deformation of the target supporting member, etc.

In response to the variation of the dosage of the X-rays applied to an object to be inspected varies, the image of the X-rays transmitted through the object changes. In such a case, it cannot be distinguished whether this change is due to characteristics of the object or due to change in the applied X-rays, and thus the object cannot be inspected precisely.

In order to overcome this difficulty, Japanese Published Unexamined Patent Application No. S55-124997 discloses an X-ray generator which monitors the dosage of X-rays emitted from an exit window of an X-ray tube using a semiconductor X-ray detector and keeps the X-ray dosage constant by the feedback of the output of the detector.

DISCLOSURE OF THE INVENTION

In recent years, inspections of electronic parts and other compact, high-density objects by means of X-rays have come to be carried out, and in accompaniment, the obtaining of X-ray images of high magnification has come to be desired. However, with the X-ray generator of Japanese Published Unexamined Patent Application No. S55-124997, though the variation of the X-ray dosage can be reduced, it is difficult to obtain X-ray images of high magnification.

In view of overcoming such a difficulty, it is an object of the present invention to provide an X-ray generator capable of keeping the X-ray dosage constant and acquiring X-ray images of high magnification.

An X-ray generator in accordance with the present invention comprises: an electron gun emitting an electron beam; an X-ray generating target positioned so that the electron beam from the electron gun is incident thereon; a first exit window transmitting an X-ray emitted from the target in response to the incidence of the electron beam; and an X-ray monitor receiving another X-ray from the target to monitor a state of the other X-ray. The X-ray monitor is positioned off the path on which the X-ray transmitted through the first exit window travels.

Since the state of the X-ray is monitored in real time by the X-ray monitor, it is possible to maintain the X-ray in a constant state. Since the X-ray monitor is positioned off the path on which the X-ray transmitted through the first exit window, the X-ray monitor is unlikely to obstruct the approach of an object to be inspected to the first exit window in irradiating the object with the X-ray from the first exit window. Consequently it is possible to bring the object close to the first exit window to acquire X-ray images of high magnification.

The first exit window has an exit surface from which the X-ray from the target is emitted. The X-ray monitor is positioned so as not to protrude beyond the exit surface. This makes easier to bring the object to be inspected close to the first exit window.

The X-ray generator may further comprise a second exit window transmitting the other X-ray from the target. The second exit window is positioned on an X-ray path different from an X-ray path extending from the target to the first exit window. The X-ray monitor receives the other X-ray transmitted through the second exit window. The X-ray monitor receives the other X-ray with higher intensity in comparison to the case where the X-ray monitor receives the other X-ray transmitted through a wall of a housing or other obstruction, thereby improving the monitoring precision of the other X-ray.

The second exit window is preferably positioned so as to face a portion of a surface of the target on which the electron beam is incident. Since X-rays are generated strongly at the electron beam incidence portion and vicinity thereof of the target, the X-rays enter the X-ray monitor efficiently from the second exit window positioned so as to face the portion.

The second exit window may be a stem plate holding a terminal of the electron gun and through which the terminal extends. The X-ray generator in accordance with this invention may, for example, be manufactured using an X-ray tube that includes an electron gun and a target. In an X-ray tube, a stem plate, such as that described above, is often installed to electrically couple an electron gun to a driver for the electron gun. The stem plate may be formed of a material that sufficiently transmits X-rays such as insulating ceramic. Using the stem plate as the second exit window for transmitting the other X-ray makes it possible to manufacture the X-ray generator of this invention without greatly modifying an existing X-ray tube with the stem plate.

A shutter able to block the X-ray may be installed between the second exit window and the X-ray monitor. By blocking the X-ray using the shutter when it is not necessary to control the state of the X-ray, such as immediately after starting the generation of the X-ray, the X-ray exposure of the X-ray monitor can be prevented to extend the lifetime of the X-ray monitor.

The X-ray generator may further comprise a housing in which the electron gun, first exit window, target, and X-ray monitor are installed. In this case, the structure of the X-ray generator can be simplified and installation of the X-ray generator becomes easier.

The electron gun, the X-ray monitor and the portion of the surface of the target onto which the electron beam is incident may be housed in an enclosure capable of being maintained under vacuum. In this case, the control of the temperature, humidity, etc., of the X-ray monitor is facilitated. The X-ray monitoring precision can thus be improved further. The X-ray monitor may be installed in the enclosure so as to face the part of the surface of the target on which the electron beam is incident. Since the X-ray is generated strongly at the electron beam incidence portion and vicinity thereof of the target, the X-ray efficiently enters the X-ray monitor from the second exit window positioned so as to face the portion. The X-ray monitoring precision can thereby be improved further.

The X-ray generator may further comprise an X-ray state controller to maintain the X-ray generated from said target in a constant state, such as constant dosage of the X-ray, based on the state of the other X-ray monitored by the X-ray monitor.

This invention will be made adequately clear by way of the detailed description that follows and the attached drawings. The attached drawings are simply illustrations of examples. This invention will thus not be considered as being restricted by the attached drawings.

A further range of application of this invention will become clear from the detailed description that follows. Though this detailed description and the specific examples illustrate preferred embodiments of this invention, these are simply examples since various modifications and changes within the gist and scope of this invention will become clear to those skilled in the art from the detailed description.

BEST MODES FOR CARRYING OUT THE INVENTION

Embodiments of this invention will now be described in detail with reference to the attached drawings. In the description of the drawings, the same elements will be provided with the same symbols and redundant description will be omitted.

FIRST EMBODIMENT

Figure 1:
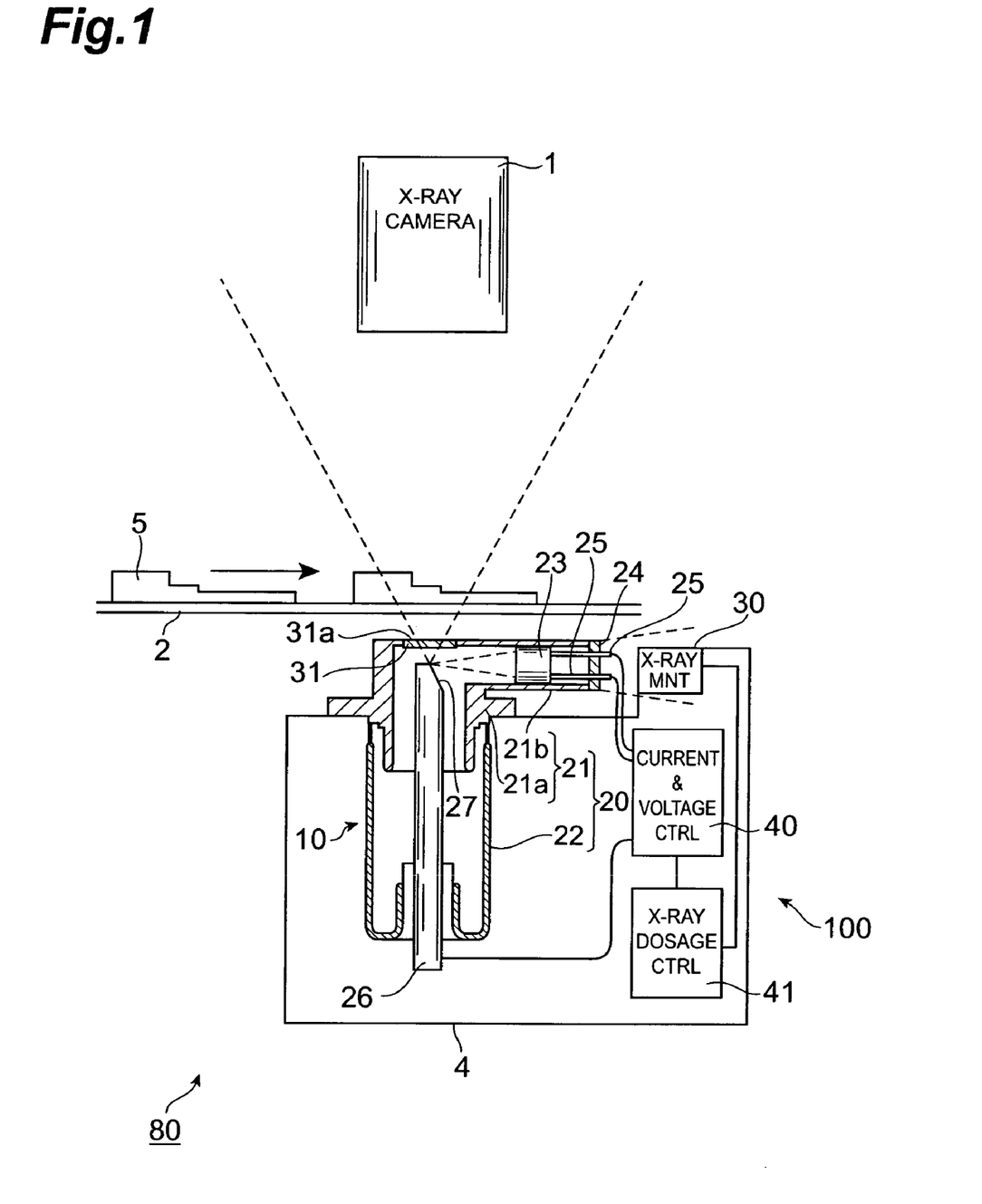
FIG. 1 is a partial sectional view showing a non-destructive inspection system having an X-ray generator of a first embodiment.

FIG. 1 is a schematic view showing a non-destructive inspection system having an X-ray generator of the first embodiment of the invention. This non-destructive inspection system 80 is for non-destructive inspection of an object 5 to be inspected. System 80 has a moving stage 2, a microfocusing type X-ray generator 100, and an X-ray camera 1. Moving stage 2 is able to be moved in horizontal directions, and a plurality of objects 5 to be inspected are placed on the top of moving stage 2. X-ray generator 100 is installed below moving stage 2 and irradiates the moving stage 2 with X-rays. X-ray camera 1 detects the X-rays transmitted through moving stage 2 and object 5 to acquire X-ray images.

X-ray generator 100 has, as principal components, an X-ray tube 10, an X-ray monitor 30 and a current and voltage controller 40. X-ray tube 10 emits X-rays generated from a reflection type target 27 upwardly. X-ray monitor 30 measures the dosage of the X-rays generated at X-ray tube 10. Current and voltage controller 40 is a driver for X-ray tube 10 and cause X-ray tube 10 to generate the X-rays by supplying a predetermined voltage and current to X-ray tube 10.

The outer shell of X-ray tube 10 is configured as a vacuum enclosure 20 of substantially cylindrical shape. Vacuum enclosure 20 extends vertically and is sealed to be maintained in a substantially vacuum state. The upper part of vacuum enclosure 20 is a main enclosure body 21 which is formed of copper or other metal. Main enclosure body 21 has a trunk part 21a which has a vertically cylindrical shape and houses reflection type target 27. Main enclosure body 21 also includes an electron gun housing cylinder 21b which has a horizontally cylindrical shape and is connected perpendicularly to trunk part 21a. Trunk part 21a and electron gun housing cylinder 21b are in communication with each other.

A ceramic stem plate 24 is installed at the end of electron gun housing cylinder 21b at the side away from the trunk part 21a. As will be described later, stem plate 24 allows the transmission of the X-rays emitted from target 27. In electron gun housing cylinder 21b, an electron gun 23 which emits an electron beam substantially horizontally towards the central axis of trunk part 21 is installed. Electron gun 23 is supported by a stem pin 25 held by stem plate 24 while extending through stem plate 24. Stem pin 25 is a terminal for supplying the driving power for electron gun 23. Stem pin 25 is electrically coupled to an electrode, filament, etc., inside electron gun 23 and is electrically coupled to current and voltage controller 40. Current and voltage controller 40 supplies the predetermined current and voltage to electron gun 23 via stem pin 25 to drive electron gun 23.

The lower part of enclosure 20 is a valve 22 which is formed of glass, ceramic, or other electric insulator. Valve 22 has a substantially cylindrical shape that is coaxial to trunk part 21a, and is connected to trunk part 21a. An electrically conductive target support 26 of substantially cylindrical form is inserted in valve 22 along the central axis of valve 22 from the lower end of valve 22. Target support 26 extends to the vicinity of the upper end of trunk part 21a.

A portion of target support 26 at its upper end on which the electron beam from electron gun 23 is incident and the surroundings of this portion form a surface inclined downward and facing electron gun 23. Reflection type target 27, formed of tungsten, etc., is installed on this inclined surface.

Target 27 is electrically coupled to current and voltage controller 40 via target support 26. The predetermined voltage which is positive relative to electron gun 23 is applied to target 27 from control device 40.

A first exit window 31 is disposed on a part of the upper wall of trunk part 21a that faces target 27. The X-rays generated from target 27 are transmitted through first exit window 31 and emitted upward out of vacuum enclosure 20. Hereinafter, the upper surface of first exit window 31 from which the X-rays are emitted will be referred to as "X-ray exit surface 31a."

Figure 2:
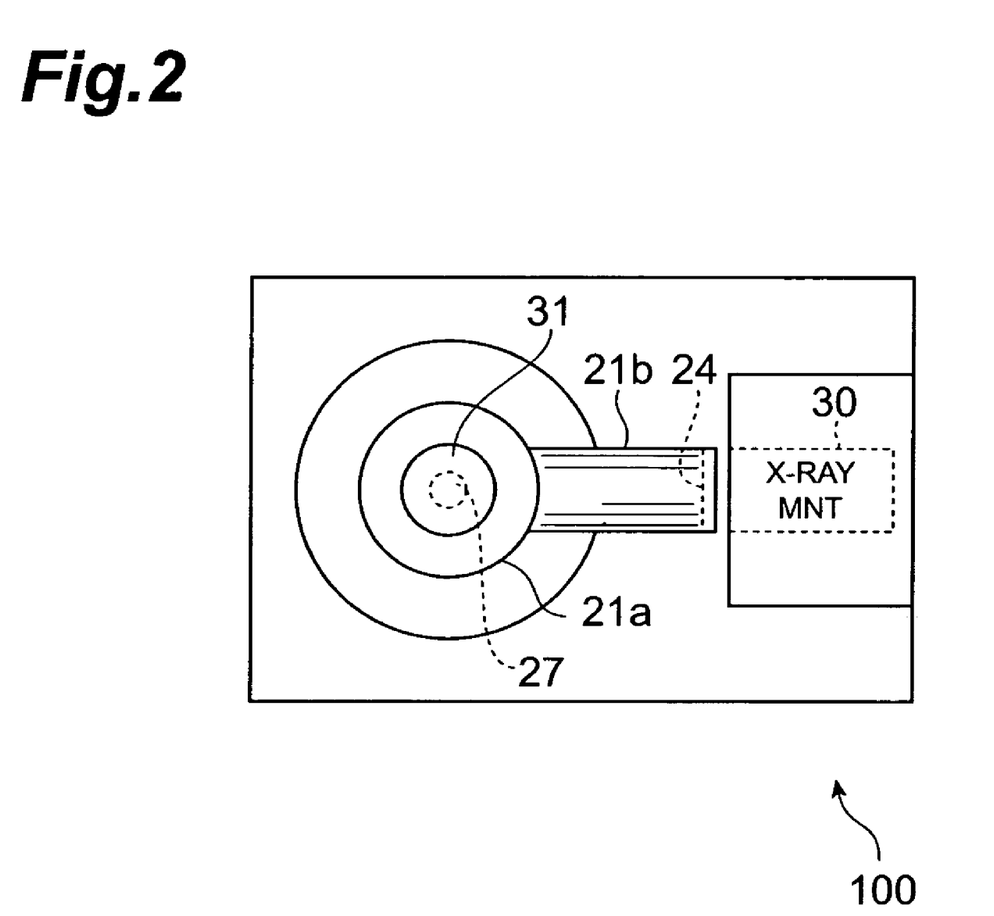
FIG. 2 is a top view of the X-ray generator shown in FIG. 1.

As shown in FIG. 1 and FIG. 2, X-ray generator 100 has X-ray monitor 30 for monitoring the dosage of the X-rays generated from target 27. X-ray monitor 30 is installed outside vacuum enclosure 20 and opposes stem plate 24. As shown in FIG. 1, X-ray monitor 30 is positioned off the path on which the X-rays emitted through first exit window 31 travel, and is positioned so as not to protrude beyond X-ray exit surface 31a. The upper surface of X-ray monitor 30 is placed below X-ray exit surface 31a, that is, at the side of target 27 from X-ray exit surface 31a. X-ray monitor 30 detects the X-rays transmitted through stem plate 24 from target 27 and measures the dosage of these X-rays in real time.

X-ray generator 100 further includes an X-ray dosage controller 41. X-ray dosage controller 41 is for controlling the state of the X-rays. X-ray dosage controller 41 controls current and voltage controller 40 so that the dosage of the X-rays generated from target 27 is constant. More specifically, controller 41 regulates the setting values of the voltage and current which current and voltage controller 40 applies to target 27 and electron gun 23 to make the X-ray dosage constant based on the X-ray dosage measured by X-ray monitor 30.

X-ray tube 10, current and voltage controller 40, X-ray dosage controller 41, and X-ray monitor 30 are all installed inside a housing 4 so as to simplify the structure of X-ray generator 100 and reduce the installation cost.

The operations and merits of non-destructive inspection system 80 and X-ray generator 100 will now be described.

When the predetermined current and voltage are applied to electron gun 23 and target 27 in X-ray tube 10 by current and voltage controller 40, an electron beam is emitted from electron gun 23. The electron beam is incident on target 27 to generate X-rays. Meanwhile, the desired object 5 to be inspected is placed on stage 2 and then stage 2 is moved so that the object 5 opposes first exit window 31.

The X-rays emitted from target 27 are transmitted through first exit window 31 in a direction that is rotated by substantially 90° with respect to the traveling direction of the electron beam and then transmitted through moving stage 2 and object 5. The transmitted X-rays are detected by X-ray camera 1 and an X-ray image is taken. By visual inspection of this X-ray image or by application of a binarization process or other image processing on the X-ray image, non-destructive inspection of object 5 is carried out.

In the present embodiment, the dosage of the X-rays generated from target 27 is monitored in real time by X-ray monitor 30. Based on the dosage monitored by monitor 30, X-ray dosage controller 41 controls current and voltage controller 40 so that the dosage of the X-rays generated from target 27 is constant. As a result, even if the dosage of the X-rays generated from target 27 varies due to thermal expansion of target support 26 caused by the heat generation of target 27, damage of the surface of target 27 by electron beam irradiation, an unpredicted variation of current or voltage, etc., this variation will be immediately feedback corrected. Hence, the dosage of the X-rays illuminated from the first exit window 31 to object 5 is made constant. Correspondingly, the background of the X-ray image that is acquired by X-ray camera 1 becomes substantially constant. Visual inspection based on this X-ray image can thus be carried out favorably. Also, in the case where inspection is carried out upon image processing the X-ray image, the setting of an optimal threshold value, etc., is facilitated. In either case, non-destructive inspection using an X-ray image can be carried out advantageously.

Since X-ray monitor 30 is positioned so as not to protrude beyond X-ray exit surface 31a, X-ray monitor 30 will not obstruct moving stage 2 and object 5, which oppose X-ray exit surface 31a, from approaching X-ray exit surface 31a. This enables moving stage 2 and object 5 to be positioned close to X-ray exit surface 31a. Hence X-ray images of high magnification can be acquired using X-ray camera 1. This is especially beneficial for non-destructive inspection of electronic components or other compact, high-density objects.

In the present embodiment, a so-called reflection type X-ray tube 10 is used. Reflection type X-ray tube 10 normally has stem plate 24 which holds stem pin 25 for supplying electric power from the outside to electron gun 23 inside X-ray tube 10. As shown in FIG. 1, stem plate 24 is positioned on an X-ray path that differs from the X-ray path directed from target 27 to first exit window 31. In the present embodiment, stem plate 24 is used as a second exit window for transmitting the monitoring X-rays. Consequently, X-ray monitor 30 can detect X-rays at higher intensity than in the case where the X-rays from target 27 are received upon passage through a wall of housing 4 or other obstacle. This improves the precision of the X-ray monitoring. Further, X-ray generator 100 of this embodiment can be manufactured without modifying a conventional X-ray tube.

SECOND EMBODIMENT

Figure 3:
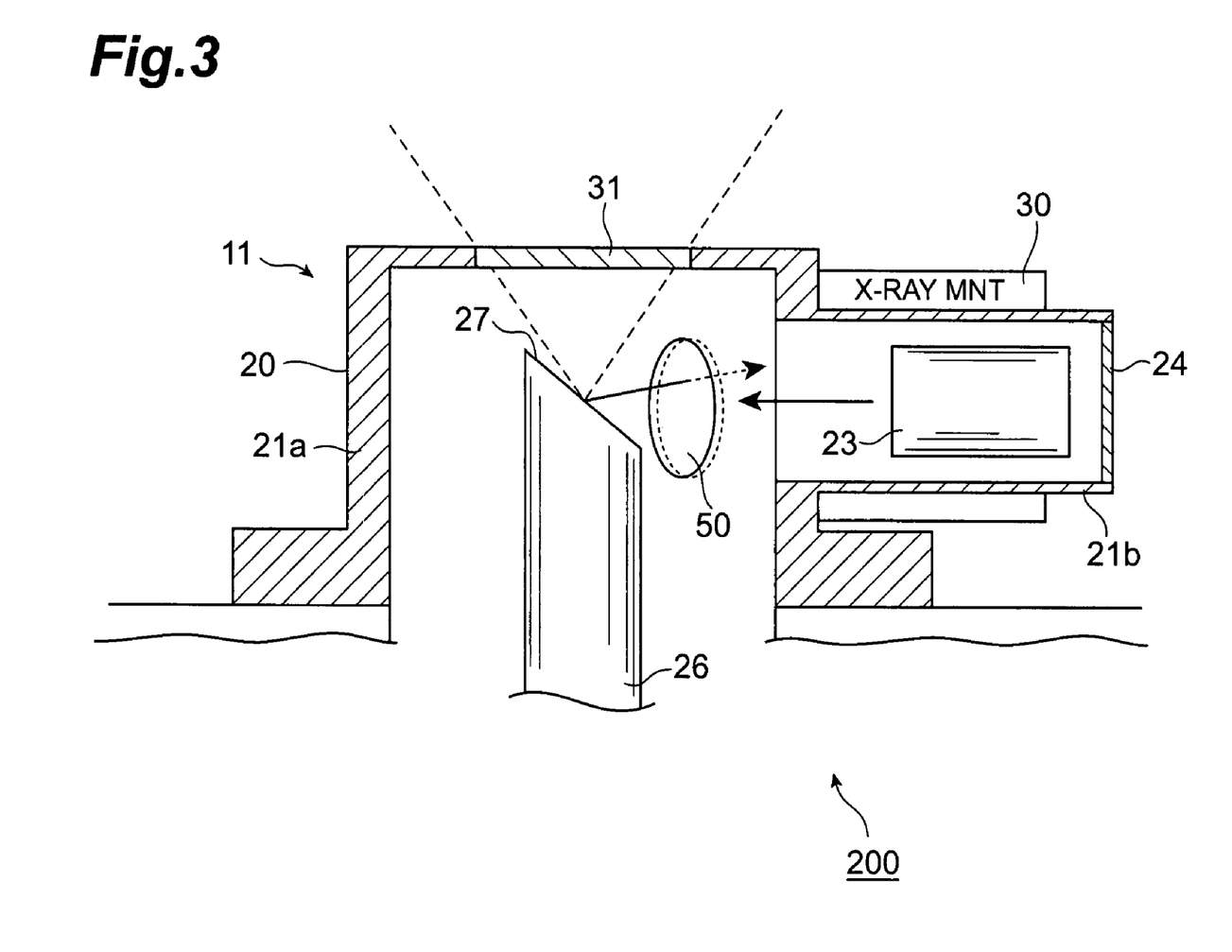
FIG. 3 is a longitudinal sectional view showing the surroundings of a target of an X-ray generator of a second embodiment.

An X-ray generator 200 of the second embodiment will now be described with reference to FIGS. 3 and 4. X-ray generator 200 differs from X-ray generator 100 of the first embodiment in having an X-ray tube 11 in place of X-ray tube 10. X-ray tube 11 has a second exit window 50 for transmitting X-rays from reflection type target 27 to the outside. Accordingly, X-ray monitor 30 does not oppose stem plate 24 but opposes second exit window 50.

Second exit window 50 is formed of Be or other substance with high X-ray transmittance and is fitted into a side wall of trunk part 21a of vacuum enclosure 20. The position of second exit window 50 is not restricted in particular; however, it is preferably installed at a position that faces the portion of the surface of target 27 on which the electron beam is incident so that X-rays with adequate intensity emerges through it.

Figure 4:
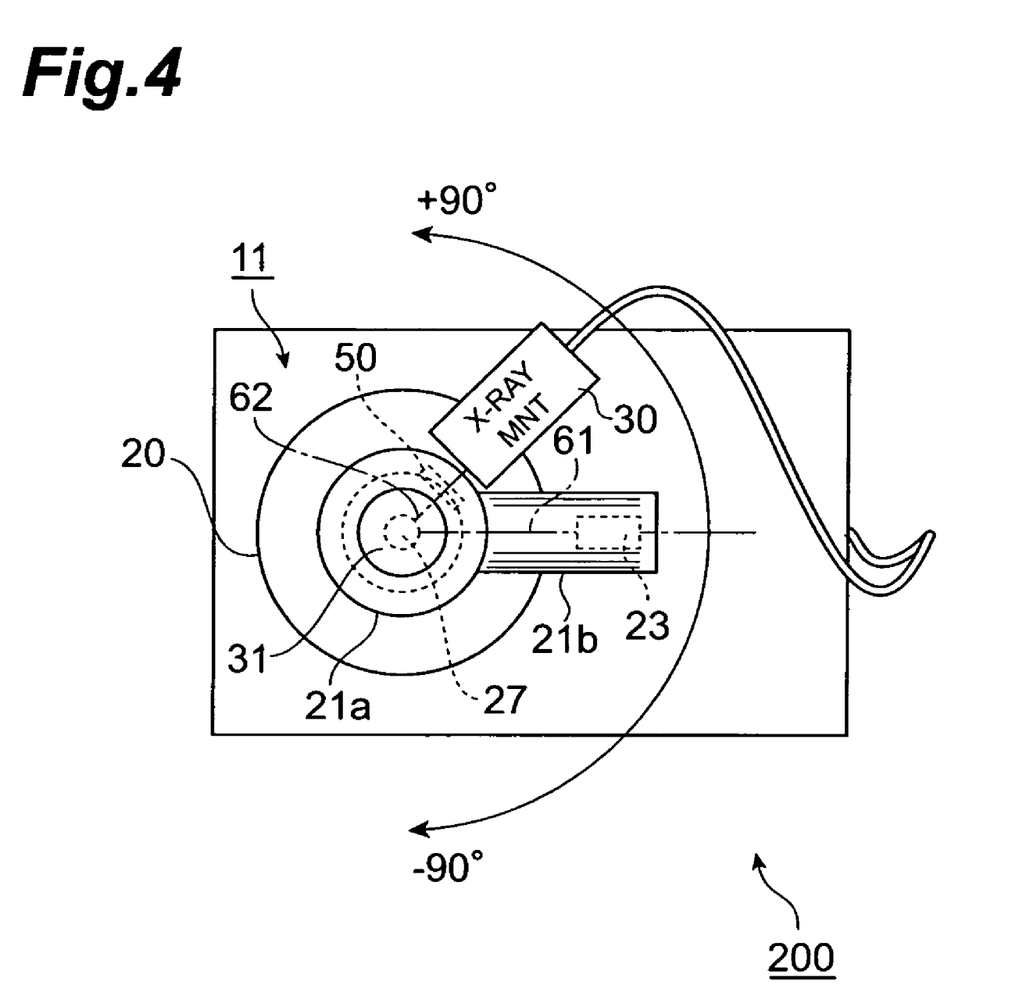
FIG. 4 is a top view of the X-ray generator shown in FIG. 3.

A preferable arrangement of second exit window 50 and X-ray monitor 30 is shown specifically in FIG. 4. X-ray monitor 30 is preferably located at a position where the angle formed by a straight line 61 extending between target 27 and electron gun 23 and a straight line 62 extending between target 27 and X-ray monitor 30 is in the range of ±90° when X-ray tube 11 is viewed from above. Second exit window 50 is preferably located at a position where straight line 62 passes when straight line 62 is positioned within ±90° from straight line 61.

In X-ray generator 200, X-rays emitted from target 27 pass through second exit window 50 and enters X-ray monitor 30 with intensity greater than or equivalent to the intensity of the X-rays emitted through stem plate 24 in the first embodiment. X-ray monitor 30 can thus monitor the state of the X-rays at high precision in the present embodiment.

THIRD EMBODIMENT

Figure 5:
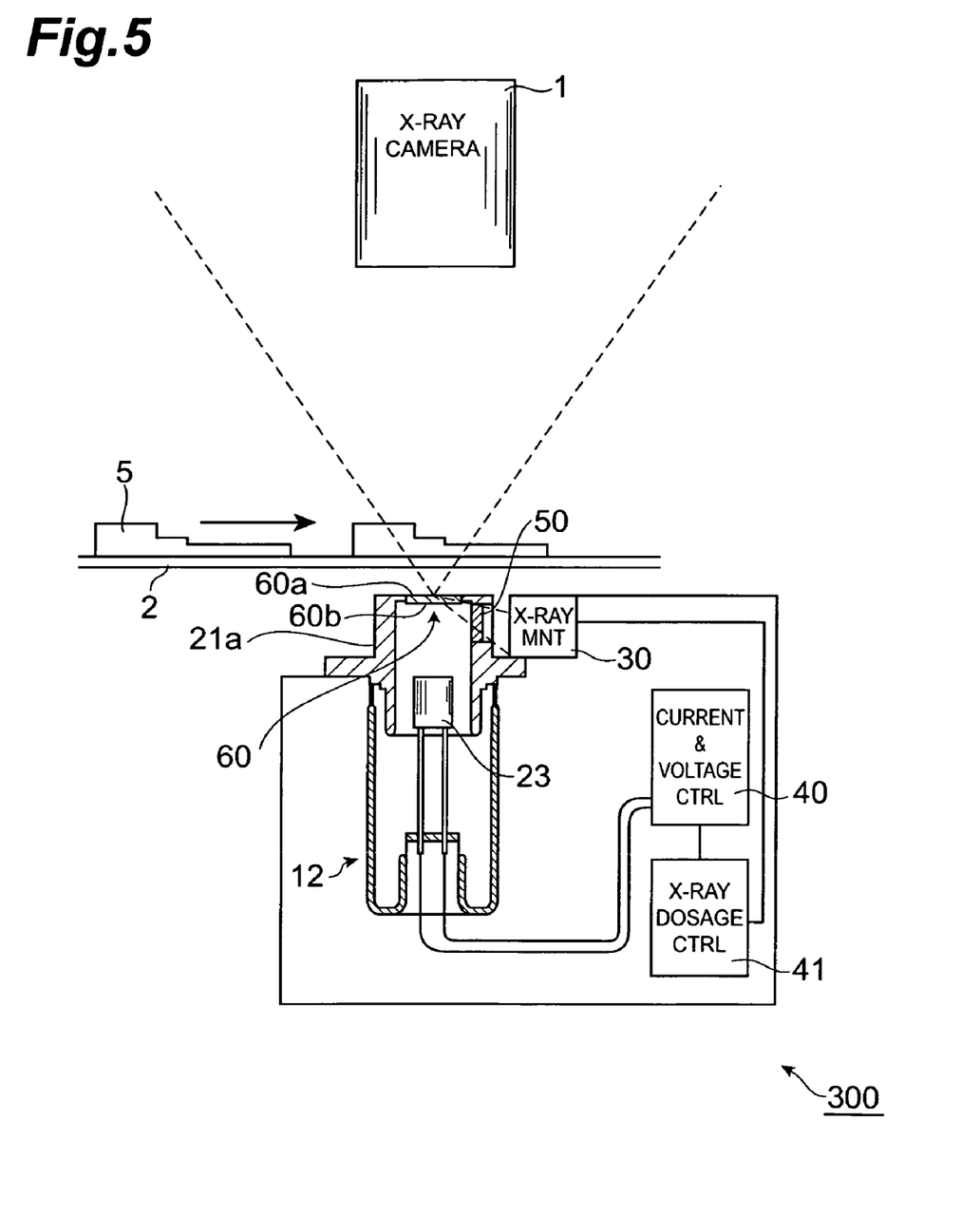
FIG. 5 is a partial sectional view showing a non-destructive inspection system having an X-ray generator of a third embodiment.

An X-ray generator 300 of the third embodiment will now be described with reference to FIG. 5. X-ray generator 300 differs from the second embodiment in having a transmission type X-ray tube 12 in place of reflection type X-ray tube 11. X-ray tube 12 has, in place of reflection type target 27 and first exit window 31 in X-ray tube 11, a transmission type target 60 which is fitted into the upper wall of trunk part 21a in substantially horizontal arrangement. Transmission type target 60 acts as both target 27 and first exit window 31 in the second embodiment. The upper surface of target 60 is an X-ray exit surface 60a and the lower surface is an electron beam incidence surface 60b.

Correspondingly, electron gun 23 is positioned below target 60 in the interior of trunk part 21a and is installed so as to emit an electron beam upward towards electron beam incidence surface 60b. Second exit window 50 is installed in the side wall of trunk part 21a so as to face electron beam incidence surface 60b.

In X-ray generator 300, the electron beam emitted from electron gun 23 enters electron beam incidence surface 60b of target 60. The X-rays generated from target 60 are emitted from X-ray exit surface 60a. Also, part of the X-rays generated from target 60 is transmitted through second exit window 50 to enter X-ray monitor 30. The dosage of the X-rays is thereby detected. Hence X-ray generator 300 with the transmission type X-ray tube 12 provides the same merits as those of the second embodiment.

FOURTH EMBODIMENT

Figure 6:
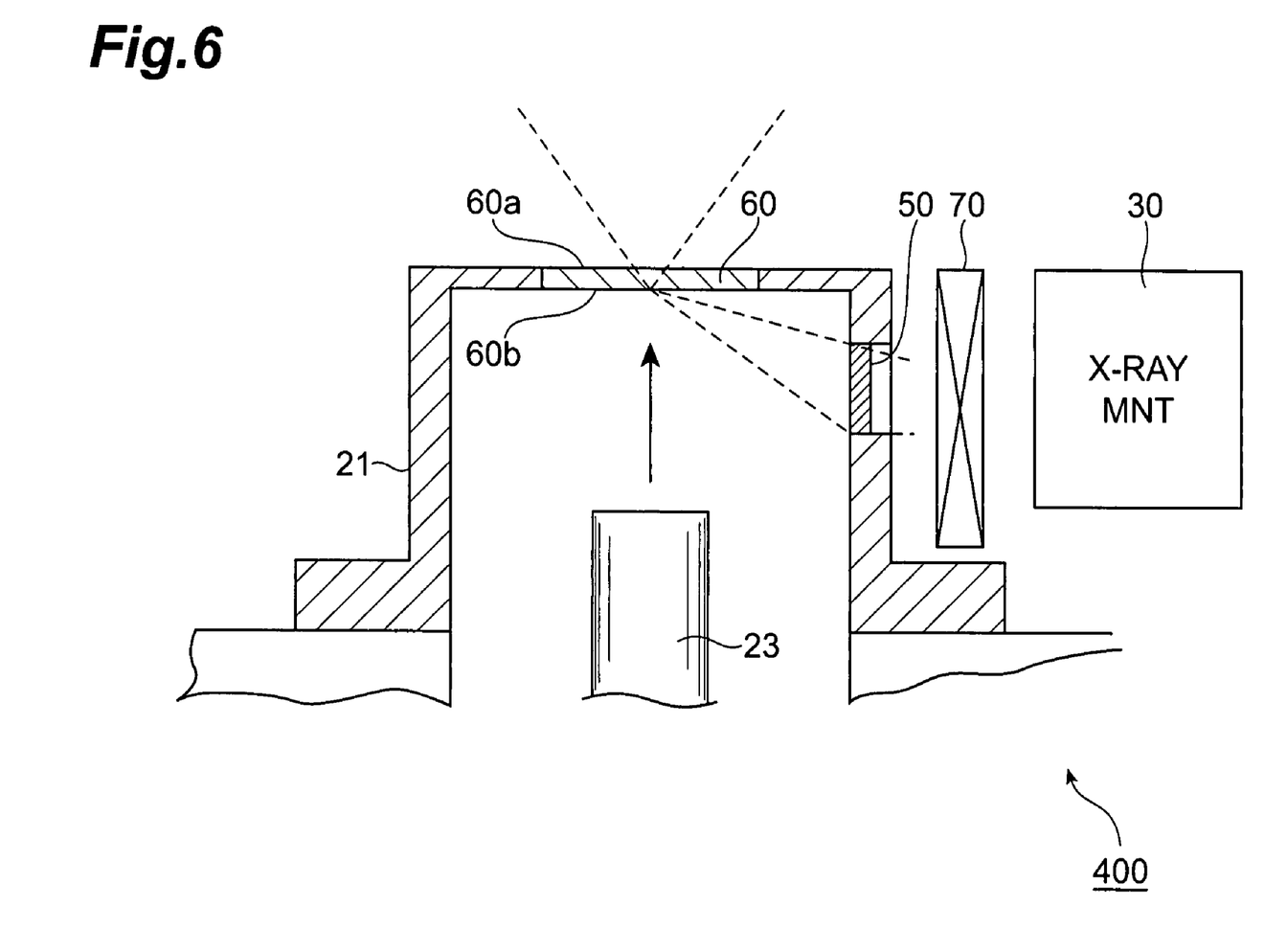
FIG. 6 is a longitudinal sectional view showing the surroundings of a target of an X-ray generator of a fourth embodiment.

An X-ray generator 400 of the fourth embodiment will now be described with reference to FIG. 6. X-ray generator 400 differs from the second and third embodiments in equipping a shutter 70 between second exit window 50 and X-ray monitor 30. Shutter 70 can block, as necessary, the X-rays emitted from second exit window 50.

By closing shutter 70 immediately after the start of generation of X-rays and other times where the control of the X-ray dosage is not required, X-rays can be blocked and prevented from entering X-ray monitor 30. This prevents the exposure of X-ray monitor 30 to extend the lifetime of X-ray monitor 30.

FIFTH EMBODIMENT

Figure 7:
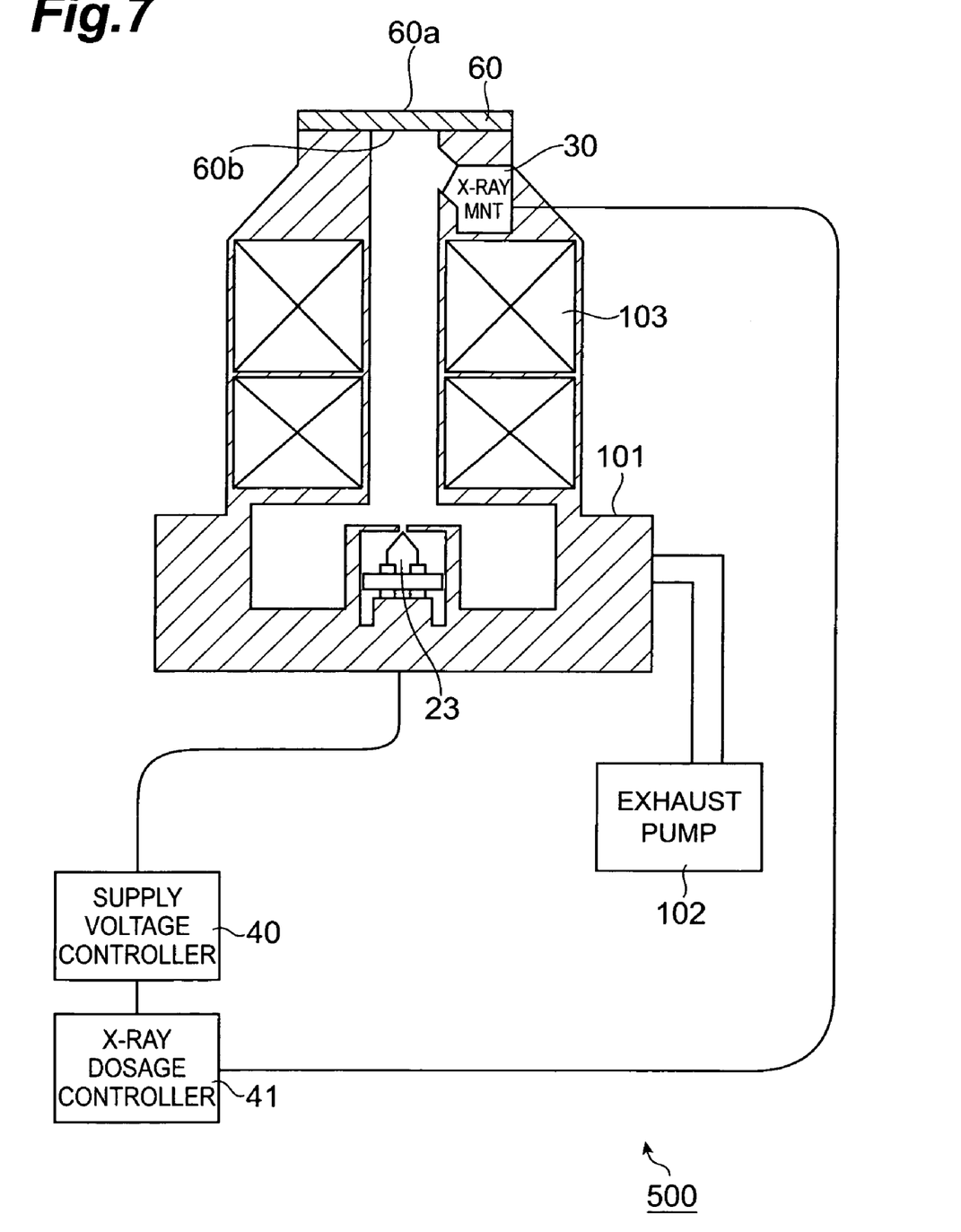
FIG. 7 is a partial sectional view showing an X-ray generator of a fifth embodiment.

An X-ray generator 500 of the fifth embodiment will now be described with reference to FIG. 7. X-ray generator 500 differs from the third and fourth embodiments in having an open enclosure 101 in place of vacuum enclosure 20 which is sealed in a vacuum state. Open enclosure 101 houses electronic beam incidence surface 60b of transmission type target 60. The interior of open enclosure 101 may be put into a vacuum state or be opened under atmospheric pressure as necessary. Open enclosure 101 is made, for example, of stainless steel.

Correspondingly, X-ray generator 500 has an exhaust pump 102 and a coil 103. Exhaust pump 102 exhausts gases in order to maintain the interior of open enclosure 101 in the vacuum state during the X-ray irradiation. Coil 103 surrounds, in an annular manner, the path of the electron beam directed from electron gun 23 to target 60, thereby adjusting the focus of the electron beam. In such a so-called open type X-ray generator, electron gun 23 and transmission type target 60 inside the generator can be exchanged.

X-ray generator 500 also differs from the third and fourth embodiments in that X-ray monitor 30 is housed inside enclosure 101. X-ray monitor 30 is preferably installed at a position facing electron beam incidence surface 60b of transmission type target 60 in the present embodiment as well.

X-ray generator 500 provides the same merits as the above-described embodiments. In addition, in X-ray generator 500, X-ray monitor 30 is housed inside open enclosure 101 and X-ray monitor 30 is thus exposed to a vacuum atmosphere during the X-ray irradiation. This facilitates the control of the temperature, humidity, etc., of the X-ray monitor and improves the precision of monitoring the state of the X-rays by the X-ray monitor.

The X-ray generator in accordance with the present invention is not restricted to the above-described embodiments and may take on various modified forms.

In the above-described embodiments, X-ray dosage controller 41 controls the output current and output voltage of current and voltage controller 40 so that the X-ray dosage is constant. However, for example, if the X-ray dosage decreases below a certain level, the controller may judge the target have reached its lifetime and deflect the electron beam so as to irradiate another portion of the target and recover the X-ray dosage to be constant. Also, the controller may automatically exchange the target.

In the above-described embodiments, X-ray monitor 30 monitors the state of the X-rays based on the X-ray dosage. However, another characteristic of the X-rays may be monitored instead. For example, in a case where a composite target containing a plurality of types of materials is employed to generate X-rays having different wavelengths, the wavelengths of the X-rays may be monitored.

In the first embodiment, stem plate 24 is made of ceramic. However, it is sufficient that stem plate 24 be made of a material that is electrically insulating and transmits X-rays sufficiently. Glass may be cited as an example of such a material.

In the second to fourth embodiments, in order to direct the X-rays generated at target 27 or 60 appropriately to X-ray monitor 30, second exit window 50 is positioned so as to face the portion of the surface of target 27 or 60 on which the electron beam is incident. However, if the X-rays emitted from reflection type target 27 are sufficiently intense, second exit window 50 may be disposed at another position.

In the first to fourth embodiments, X-ray monitor 30 may be installed inside vacuum enclosure 20 if X-ray tube 10, 11, or 12 is large, for example. In this case, as in the fifth embodiment, X-ray monitor 30 is preferably installed so as to face the electron beam incidence surface of the target. In the fifth embodiment, X-ray monitor 30 may be positioned outside open enclosure 101 and receive the X-rays through the second exit window provided on open enclosure 101.

In the first to fourth embodiments, in order to monitor the X-rays precisely, second exit window 50 or stem plate 24 for transmitting the X-rays is installed or X-ray monitor 30 is installed inside open enclosure 101. However, if the X-rays generated from the target are intense, for example, the state of the X-rays transmitted through the enclosure to the outside without passing through a window or the like may be monitored by X-ray monitor 30 outside the enclosure.

In the above-described embodiments, an image of the X-rays transmitted through object 5 to be inspected is taken. However, for example, a tomographic image may be taken by CT. In this case, since the magnification is high and the computing is carried out based on the X-ray image obtained with the stable X-rays, the precision of tomography is improved.

INDUSTRIAL APPLICABILITY

As described above, X-ray generators in accordance with the present invention can monitor the state of the X-rays emitted from the target in real time using the X-ray monitor. It is possible to maintain the X-rays generated from the target in a constant state by controlling the current and voltage applied to the electron gun and the target, or moving the electron beam incidence position on the target, or other regulation, according to the state of the X-rays acquired by the X-ray monitor. Consequently, the generators can emit stable X-rays from the first exit window.

The X-ray monitor is positioned off the path on which the X-rays travel from the target to enter the first exit window. Thus, when X-rays are emitted through the first exit window to an object to be inspected, the X-ray monitor is not likely to obstruct approach of the object to the first exit window. Hence it is possible to bring the object close to the first exit window, thereby obtaining X-ray images of high magnification.

Thus this invention provides the X-ray generator capable of keeping the X-ray dosage constant and acquiring X-ray images of high magnification.

The invention claimed is:

1. An X-ray generator comprising:
   an X-ray tube comprising:
   a vacuum enclosure (20);
   an electron gun (23) provided in the vacuum enclosure (20) and emitting an electron beam in an electron beam direction; and
   an X-ray generating target (26) having an electron incident surface (27) onto which the electron beam emitted from the electron gun (23) enters; and an X-ray monitor (30) for receiving the X-rays to monitor the received X-rays,
   wherein the vacuum enclosure has first and second exit windows which constitute a part of the vacuum enclosure respectively,
   wherein the vacuum enclosure (20) has a metal housing (21) in which the first (31) and second (24) windows are independently and respectively provided on the metal housing (21),
   wherein the electron incident surface (27) of the X-ray generating target (26) is provided within the metal housing (21);
   wherein the first (31) and second (24) windows are separated through a part of the metal housing (21);
   wherein an X-ray exiting direction of the X-rays through the first window and an X-ray exiting direction of the X-rays through the second window intersect each other, and
   wherein the X-ray exiting portion of the second window and the X-ray monitor (30) are positioned so that the X-ray exiting portion of the second window (24) and the X-ray monitor are in the vacuum enclosure side with respect to a plane (31*a*) of an exit surface of the first window (31), wherein
   the electron incident surface of the X-ray generating target is supported in an inner space of the metal housing without contacting the metal housing by a target support,
   the metal housing (21) has an electron gun storing portion (21*b*) which projects from a main body (21*a*) of the metal housing (21),
   a stem plate (24) made of ceramics is provided at an edge portion of the electron gun storing portion (21*b*),
   a stem pin (25) holding the electron gun (23) passes through the stem plate (24),
   the stem pin (25) holds the stem plate (24),
   the stem plate (24) functions as the second window (24) and faces to the X-ray monitor, and
   the X-ray monitor is positioned so that the X-ray monitor is in the vacuum enclosure side with respect to the plane (31*a*) of an exit surface of the first window (31).

* * * * *